United States Patent [19]

Yasuda et al.

[11] 4,361,560
[45] Nov. 30, 1982

[54] IMIDAZOLEDICARBOXYLIC ACID DERIVATIVE

[75] Inventors: Naohiko Yasuda, Yokosuka; Chikahiko Eguchi, Yokohama; Masaru Okutsu, Yamato; Yoshiteru Hirose, Kamakura, all of Japan

[73] Assignee: Ajinomoto Company Incorporated, Tokyo, Japan

[21] Appl. No.: 187,754

[22] Filed: Sep. 16, 1980

Related U.S. Application Data

[62] Division of Ser. No. 134,681, Mar. 27, 1980, Pat. No. 4,297,279.

[30] Foreign Application Priority Data

Mar. 27, 1979 [JP] Japan .................................. 54-36133

[51] Int. Cl.³ .................. C07D 501/38; A61K 31/545
[52] U.S. Cl. ...................................... 424/246; 544/25; 544/28
[58] Field of Search ...................... 544/21, 26, 25, 27; 424/246

[56] References Cited

U.S. PATENT DOCUMENTS

| | | | |
|---|---|---|---|
| 3,449,338 | 6/1969 | Flynn | 544/25 |
| 3,646,024 | 2/1972 | Holdrege | 544/25 |
| 4,217,450 | 8/1980 | Yasuda et al. | 544/25 |

Primary Examiner—Nicholas S. Rizzo
Attorney, Agent, or Firm—Oblon, Fisher, Spivak, McClelland & Maier

[57] ABSTRACT

An imidazoledicarboxylic acid derivative having the following formula:

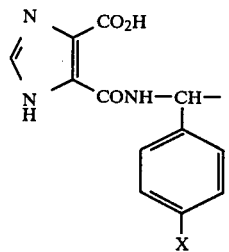

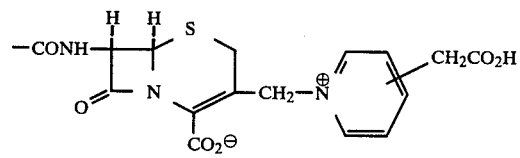

wherein X is a group selected from the group consisting of hydrogen atom and hydroxyl group. The compounds are useful as antibiotics.

6 Claims, No Drawings

IMIDAZOLEDICARBOXYLIC ACID DERIVATIVE

This application is a divisional and continuation-in-part of copending application Ser. No. 134,681, filed Mar. 27, 1980, now U.S. Pat. No. 4,297,279.

BACKGROUND OF THE INVENTION

The present invention relates to novel imidazoledicarboxylic acid derivative, which is useful as antibiotics, particularly, for oral administration, particularly as antibacterial agent in the treatment of *Pseudomonas aeruginosa* infectious diseases in both human beings and other animals.

SUMMARY OF THE INVENTION

The present inventors have succeeded in synthesizing novel imidazoledicarboxylic acid derivative, having the following formula:

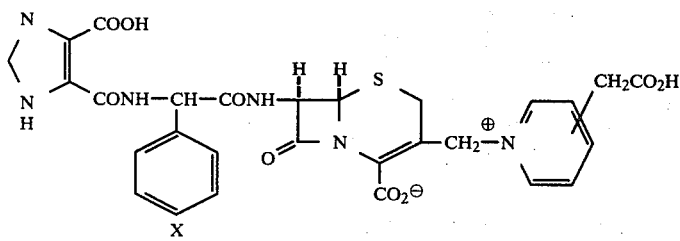

wherein X is a group selected from the group consisting of hydrogen atom and hydroxyl group, and pharmaceutically acceptable nontoxic salts thereof, and have discovered that these novel compounds have a good antibacterial activity and oral absorption, particularly against *Pseudomonas aeruginosa* and can be used as antibiotics, particularly for oral administration.

DESCRIPTION OF THE PREFERRED EMBODIMENTS

The amino acid which forms the compounds of the present invention is phenylglycine, or 4-hydroxyphenylglycine which may be in the L-, D-form, or DL-form.

In many cases, D-form is suitable in view of antibacterial activity.

Suitable pharmaceutically acceptable salts of such compounds are conventional non-toxic salts and may include metal salts such as alkali metal salt (e.g., sodium salt, potassium salt, etc.) or an alkaline earth metal salt (e.g., calcium salt, magnesium salt, etc.), ammonium salts, organic amine salts (e.g., trimethylamine salt, triethylamine salt, pyridine salt, picoline salt, dicyclohexyl amine salt, N,N'-dibenzylethylene diamine salt, procain salt, dibenzylammonium salt, N-benzyl-β-phenylammonium salt and salt with amino acid such as L-lysine etc.) and the like.

Such salts of the present invention are prepared by conventional methods, for example by neutralizing the free base form of a compound of the present invention with alkali.

The imidazoledicarboxylic acid derivative of the present invention has effective antibacterial activity against not only gram positive and gram negative bacteria but also *Pseudomonas aeruginosa* and has good oral absorption, and therefore, can be practically used as medicines for human beings and the other animals, particularly for oral administration.

The imidazoledicarboxylic acid derivative of the present invention can be prepared by reacting a compound having the formula:

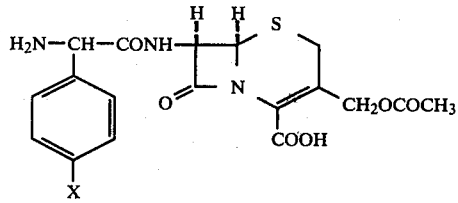

with an imidazoledicarboxylic acid having the formula:

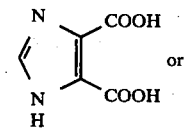

its reactive derivative such as the acid chloride derivative and a compound having the formula:

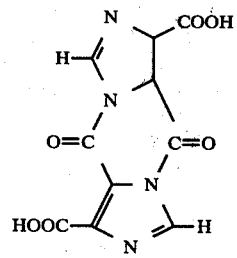

to produce a compound having the formula:

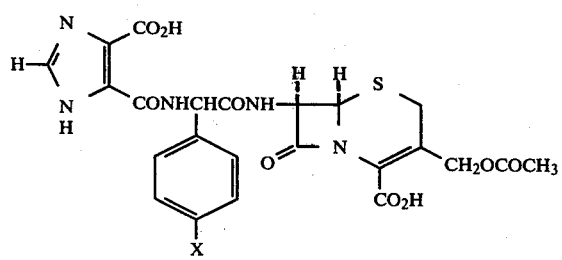

and reacting the compound with carboxymethylpyridine having the formula:

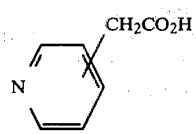

In such formulas, X has the same meaning as above.

The reaction of the carboxymethylpyridine can be carried out in the presence of catalyst such as KI, KSCN, and NaI, preferably, in the solvent such as water or a mixture of water and hydrophilic organic solvent such as acetone, acetonitrile, methanol, ethanol tetrahydrofuran, dimethylformamide.

Preferably, such reaction is carried out at PH 5 to 8, and at a temperature of 30° C. to 90° C.

The reaction products of the modification reaction can be isolated in pure form by known procedures, for example by extraction, column chromatography, recrystallization and the like.

The present invention is explained precisely in the following Examples.

EXAMPLE 1

Imidazole-4,5-dicarboxylic acid (3.12 g, 20 mM) was suspended in dry benzene (40 ml) containing DMF (6 drops). To this mixture thionyl chloride (8 ml) was added. The thus obtained mixture was stirred at 85° C. for 5.5 hours under reflux. The mixture was concentrated to yield solid material under reduced pressure. And the acid chloride derivative produced thereby was suspended in dry dichloromethane (40 ml).

Anhydrous 7-β-[D-(−)-α-aminophenylacetamido]-cephalosporanic acid (4.05 g, 10 mM) was suspended in dichloromethane (40 ml). To this mixture triethyl amine (14 ml) was added and thereby a homogeneous solution was prepared.

7-β-[D-(−)-α-aminophenylacetamido]cephalosporanic acid dichloromethane solution was added stepwise little by little to the acid chloride derivative dichloromethane suspension prepared above in an ice bath while stirring over a period of 15 minutes. After addition of the 7-β-[D-(−)-α-aminophenylacetamido]-cephalosporanic acid, the mixture was further stirred for two hours in the ice bath. Insoluble material was removed by filtration, and the solution was concentrated at less than 30° C. under reduced pressure to yield solid material. The thus obtained solid material was dissolved in water (70 ml). To this mixture ethyl acetate (70 ml) was added and thereby a solution having two layers was prepared. The water solution was separated and to this solution ethyl acetate (100 ml) was added. 6% Hydrochloric acid was added to the mixture while stirring and thereby the water phase of the solution was adjusted to PH 2. The precipitate was removed by filtration and a solution having two layers was obtained. The water solution was separated and extracted with ethyl acetate (100 ml), once more. The ethyl acetate solutions obtained were combined and dried with anhydrous magnesium sulphate. The ethyl acetate solution was concentrated at less than 30° C. and the solid material thus obtained was triturated by adding ether (100 ml) thereto, and separated by filtration. The powdered material was dried to give 7-β-[D-(−)-α-(4-carboxyimidazole-5-carboxamido)phenylacetamido]cephalosporanic acid monohydrate (1.87 g, yield: 34.4%).

M.P., 209°–218° C. (dec.).

Elemental analysis: Found: C 49.66%, H 3.98%, N 12.77%, S 5.66%. Calcd. for $C_{23}H_{21}N_5O_9S \cdot 1H_2O$: C 49.19%, H 4.14%, N 12.47%, S 5.71%.

TLC (silica gel): $R_f = 0.70$.

I.R. spectrum (Nujol): $\nu_{CO}(\beta\text{-lactam}) = 1775$ cm$^{-1}$, $\nu_{CO}(-OCOCH_3) = 1745$ cm$^{-1}$.

Thus obtained 7-β-[D(−)-α-(4-carboxyimidazole-5-carboxyamide)phenylacetamide]-cephalosporanic acid (16.3 g, 30 mM) and 3-pyridylacetic acid (8.2 g, 60 mM) were suspended in water (150 ml), and to this mixture 2 N—NaOH aqueous solution was added dropwise, slowly to dissolve such starting materials, and then the solution was adjusted to PH 7.5. To the thus obtained solution sodium iodide (120 g, 0.8 M) was added and the thus obtained mixture was reacted while stirring at 70° C. for 2 hours. After completion of the reaction, the reaction solution was passed through the column of Amberlite XAD-2 (2 l) produced by Rhom & Haas for absorption of the desired product. By elution with water, fractions containing the desired product were collected and freeze-dried.

The thus obtained solid material (10.4 g) was dissolved in water (50 ml), and thereto ethanol (250 ml) was added slowly dropwise while stirring and being cooled to precipitate a solid material. Such mixture was stood in the refrigerator overnight, and then the precipitated solid material was obtained by filtration and dried. The thus obtained solid material (5.5 g) was dissolved in water (20 ml) and the solution was passed through the column of Amberlite XAD-7 (700 ml) for absorption of the desired product. By elution with water, fractions containing the desired product were collected and freezedried to give the desired product, (7-β-[D(−)-α-(4-carboxyimidazole-5-carboxyamide)-phenylacetamide]-3-(3-carboxymethylpyridinium)-methyl-3-cephem-4-carboxylic acid disodium salt (3.6 g, yield: 19%).

I.R. spectrum (Nujol): $\nu C = O$ (β-lactam) = 1760 cm$^{-1}$.

N.M.R. spectrum (D$_2$O, δ)

ppm 3.25 (q, 2H) (>CH$_2$, 2-position)

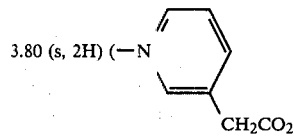

3.80 (s, 2H) (—N 5.12 (d, 1H) (—H, 6-position)

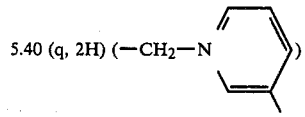

5.40 (q, 2H) (—CH$_2$—N )

5.62 (S, 1H) (—CH—)

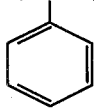

5.80 (d, 1H) (—H, 7-position)

7.50 (m, 5H) ( 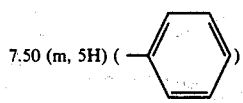 )

7.83 (S, 1H) (—H, 2-position of imidazole)
8.00, 8.46, 8.82 (4H) (—H, pyridine ring)

EXAMPLE 2

Imidazoledicarboxylic acid (7.8 g, 0.05 M) was suspended in dry benzene (100 ml), and thereto DMF (4 ml) and then thionyl chloride (30 ml) were added. The thus obtained mixture was refluxed at a temperature of 85° C. while stirring. After completion of the reaction, the reaction mixture was concentrated to yield solid material. To the thus obtained material, dry benzene (50 ml) was added and the mixture was concentrated to yield solid material, once more. To the remaining material benzene (50 ml) was added and the mixture was stirred at room temperature for 30 minutes. Insoluble solid material was collected by filtration and then washed with benzene and dried under reduced pressure to give the desired product, 5,10-dioxo-5,10-dihydrodiimidazo [1,5a,1′,5′ d]pyrazine-1,6-dicarboxylic acid dichloride (7.0 g, yield: 89%).

Elemental analysis: Found: C 38.03%, H 0.74%, N 17.81%, Cl 22.37%. Calcd. as $C_{10}H_2N_4O_4Cl_2$: C 38.36%, H 0.64%, N 17.90%, Cl 22.65%.

The thus obtained acid chloride (7.0 g) was suspended in water (150 ml) and the mixture was stirred at 10°–20° C. overnight. An insoluble solid material was obtained by filtration and washed with water, a small amount of THF, and then ether. The material was dried under reduced pressure to give the desired product, 5,10-dioxo-5,10-dihydrodiimidazo [1,5a,1′,5′ d]pyrazine-1,6-dicarboxylic acid dihydrate (7.0 g, yield: 100%).

M.P., 284° C. (dec.).

I.R. spectrum: 3500 cm$^{-1}$, 1750 cm$^{-1}$, 1710 cm$^{-1}$, 1255 cm$^{-1}$, 930 cm$^{-1}$.

Elemental analysis: Found: C 38.65%, H 2.40%, N 18.02%. Calcd. as $C_{10}H_4N_4O_6 \cdot 2H_2O$: C 38.47%, H 2.58%, N 17.95%.

Anhydrous 7-β-[D(−)-α-aminophenylacetamido]-cephalosporanic acid (6.5 g, 16 mM) was suspended in dry dichloromethane (100 ml) and triethylamine (6 ml) was added thereto. The mixture was stirred for 30 minutes while being cooled with ice-water. To this solution 5,10-dioxo-5,10-dihydrodiimidazo [1,5a,1′,5′ d]pyrazine-1,6-dicarboxylic acid dihydrate (2.2 g, 7 mM) was added while stirring and cooling. The mixture was stirred overnight, and concentrated to give solid material. This material was added to water (50 ml) and stirred to give a homogeneous solution. The solution was adjusted to PH 8 with 6% aqueous HCl solution, stirred for 10 minutes, and then washed with ethyl acetate (50 ml). The water phase was adjusted to PH 2 with 6% aqueous HCl solution, and the mixture was stirred for 20 minutes. The precipitated crystalline material was collected by filtration, washed with water, and then dried under reduced pressure at 40° C. The thus obtained solid material was suspended in a solvent (500 ml) obtained by mixing ethylacetate and methanol (volume ratio: 1/1), and the mixture was stirred at 40° C. for 20 minutes. An insoluble material was separated by filtration. Thus obtained organic phase was concentrated under reduced pressure to volume of 50 ml, and ether (500 ml) was added thereto. This mixture was left overnight in the refrigerator. Thus precipitated crystals were collected, washed with petroleum ether and dried to give the desired product, 7-β-[D(−)-α-(4-carboxyimidazole-5-carboxamido)-phenylacetamido]cephalosporanic acid (6.5 g, yield: 75%).

Hereinafter, 7-β-[D(−)-α-(4-carboxyimidazole-5-carboxyamido)-phenylacetamido]-3-(3-carboxymethylpyridinium)-methyl-3-cephem-4-carboxylic acid disodium salt was obtained in the same manner as in Example 1.

As regards the compound produced in Example 1 described above, anti-bacterial activities were determined. Some of them were shown Table 1. Now, "MIC" represents the Minimum Inhibitory Concentration in μg/ml of the compound required to inhibit the growth of the test organism.

TABLE 1

| | MIC (μg/ml) | | |
|---|---|---|---|
| Microorganism | Compound in the Ex. 1 | Carbenicillin | Ampicillin |
| E. Coli | 3.13 | 3.13 | 3.13 |
| Pseudomonas aeruginosa | 3.13 | 25 | >100 |
| Klebsiella pneumoniae | 3.13 | >100 | 25 |
| Proteus Vulgaris | 12.5 | 1.56 | 25 |
| Proteus mirabilis | 3.13 | 1.56 | 3.13 |

As regards the compound produced in Example 1, oral absorption in mouse was tested and results were shown in Table 2.

[EXPERIMENT]

Concentration in Blood (μg/ml) by oral administration was obtained.

Mouse: ICR 5W ♂
Oral administration dose: 50 mg/kg
Test organism: Staph. aureus 209P

TABLE 2

| | (μg/ml) | | | |
|---|---|---|---|---|
| | Time (minutes) | | | |
| Sample | 30 | 60 | 120 | 180 |
| Compound in Example 1 | 309 | 274 | 252 | 267 |
| Cefoperazone (T-1551) | 15.6 | 24.0 | 18.2 | 23.1 |

Practical treatment by oral administration for an infectious disease of mouse was tested. Results were shown in Table 3.

[EXPERIMENT]

Mouse: 3W, IRC ♂
Bacterial challenge: Pseudomonas aeruginosa A-14 1×10$^6$/mouse i.p.

TABLE 3

| Dose | Number of Living Mouse |
|---|---|
| 0 | 0/4 |
| 6.25 mg/mouse | 4/4 |

As is evident from those above results, it is understood that imidazoledicarboxylic acid derivative of the present invention has a good practical use as medicines for human beings and other animals.

What is claimed is:

1. An imidazoledicarboxylic acid derivative having the following formula:

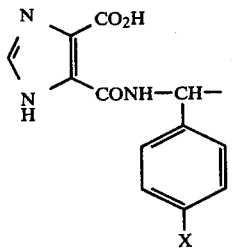

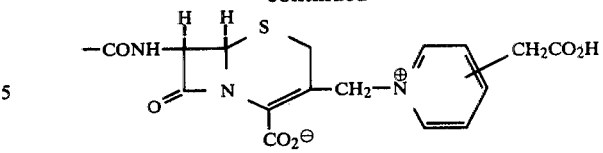

wherein X is a group selected from the group consisting of hydrogen atom and hydroxyl group.

2. An imidazole dicarboxylic acid derivative of claim 1, wherein the amino acid forming said imidazoledicarboxylic acid derivative is in the D-form.

3. An imidazole dicarboxylic acid derivative of claim 1, wherein said derivative is in the salt form.

4. A method for treating infectious deseases in mammals comprising administering to said mammal having an infectious disease a therapeutically effective amount of a compound of claim 1.

5. The method of claim 5 wherein said compound is administered orally.

6. A method for inhibiting the growth of bacteria comprising contacting said bacteria with a compound of claim 1.

* * * * *

UNITED STATES PATENT AND TRADEMARK OFFICE
CERTIFICATE OF CORRECTION

PATENT NO. : 4,361,560

DATED : November 30, 1982

INVENTOR(S) : NAOKIHO YASUDA ET AL

It is certified that error appears in the above-identified patent and that said Letters Patent is hereby corrected as shown below:

Please correct the Foreign Application Priority Data as follows:

[30] --Foreign Application Priority Data

March 27, 1979 [JP] Japan....54-36133

December 5, 1978 [JP] Japan... 53-150792 --.

Signed and Sealed this

Eighth Day of May 1984

[SEAL]

Attest:

Attesting Officer

GERALD J. MOSSINGHOFF

Commissioner of Patents and Trademarks